United States Patent
Curran et al.

(10) Patent No.: US 11,717,450 B2
(45) Date of Patent: Aug. 8, 2023

(54) SYSTEM FOR MANAGING INCONTINENCE

(71) Applicant: Fred Bergman Healthcare Pty Ltd, North Sydney (AU)

(72) Inventors: Peter Curran, North Sydney (AU); Kenneth Huynh, North Sydney (AU)

(73) Assignee: Fred Bergman Healthcare Pty Ltd, North Sydney (AU)

( * ) Notice: Subject to any disclaimer, the term of this patent is extended or adjusted under 35 U.S.C. 154(b) by 451 days.

(21) Appl. No.: 16/762,124

(22) PCT Filed: Nov. 7, 2018

(86) PCT No.: PCT/AU2018/051201
§ 371 (c)(1),
(2) Date: May 6, 2020

(87) PCT Pub. No.: WO2019/090387
PCT Pub. Date: May 16, 2019

(65) Prior Publication Data
US 2020/0352794 A1    Nov. 12, 2020

(30) Foreign Application Priority Data
Nov. 7, 2017  (AU) ................................ 2017904525

(51) Int. Cl.
*A61F 13/42* (2006.01)

(52) U.S. Cl.
CPC ........ *A61F 13/42* (2013.01); *A61F 2013/422* (2013.01); *A61F 2013/424* (2013.01)

(58) Field of Classification Search
CPC ....... G08B 21/20; G01P 13/00; G01N 27/223; G01N 27/22; G01N 27/227; A61B 5/6808;
(Continued)

(56) References Cited

U.S. PATENT DOCUMENTS

2010/0328075 A1* 12/2010 Rahamim ................ A61F 5/56
                                                      340/573.1
2013/0324955 A1* 12/2013 Wong ..................... A61F 13/42
                                                      604/361
(Continued)

FOREIGN PATENT DOCUMENTS

WO    2015/003712 A1    1/2015
WO    2015/094063 A1    6/2015
(Continued)

OTHER PUBLICATIONS

PCT/AU2018/051201 International Search Report and Written Opinion dated Jan. 30, 2019.

*Primary Examiner* — Erich G Herbermann
*Assistant Examiner* — Seth Han
(74) *Attorney, Agent, or Firm* — Wagenknecht IP Law Group PC

(57) ABSTRACT

The invention relates to an incontinence monitoring system including a plurality of electrodes on an absorbent article including an absorbent core and a device for electrical connection with the electrodes and monitoring one or more electrical properties of the electrodes. A first set of the electrodes are adapted for detection of wetness associated with urinary incontinence events, and a second set of the electrodes are adapted for detection of faecal incontinence events. The invention also relates to an absorbent article, sensor and device as well as methods for monitoring incontinence.

10 Claims, 7 Drawing Sheets

(58) Field of Classification Search
CPC .. A61B 5/6802; A61F 13/42; A61F 2013/424; A61F 13/84
See application file for complete search history.

(56) References Cited

U.S. PATENT DOCUMENTS

2017/0071803 A1* 3/2017 Wu ................. A61B 5/0205
2017/0258643 A1* 9/2017 Xu .................... A61F 13/42
2017/0296397 A1* 10/2017 Kunze ............... A61F 13/42

FOREIGN PATENT DOCUMENTS

| WO | 2016/028497 A1 | 2/2016 |
| WO | 2016/090492 A1 | 6/2016 |
| WO | 2017/143396 A1 | 8/2017 |

* cited by examiner

SYSTEM FOR MANAGING INCONTINENCE

CROSS REFERENCE TO RELATED APPLICATIONS

This is a US national phase application under 35 USC § 371 of international patent application no. PCT/AU2018/051201, filed Nov. 7, 2018, which itself claims priority to Australian patent application no. 2017904525, filed Nov. 7, 2017. Each application referred to in this paragraph is herein incorporated by reference in its entirety.

TECHNICAL FIELD

The present invention relates to a combination of sensors, a system and a method for detecting the presence of bodily excretions, such as from urine or faecal matter, in an incontinence garment, pad, diaper, or the like.

BACKGROUND OF INVENTION

Incontinence is a condition characterised by the uncontrolled release of bodily excretions from the bladder and/or bowel. Urinary incontinence refers to loss of bladder control resulting in involuntary or uncontrolled urination. Urinary incontinence is a condition that is prevalent among infants, the elderly and infirm and, at least in relation to adult sufferers, is more prevalent among women.

Incontinence is managed in the community and in care institutions such as hospitals, nursing homes, aged care facilities, child day care centres and the like by the use of absorbent articles, such as pads, diapers and the like that are worn by subjects. Periodic and manual checking is required, more particularly in institutional care, to determine whether it is the correct time to change an absorbent article worn by a subject.

Incontinence indicators and detection systems including sensors contained in absorbent articles exist. Such systems can include sensors that are adapted for electrical connection to an electronic device, such as a transceiver, which sends a signal to a processing device when an incontinence event is occurring or has occurred in the absorbent article. The system is configured to measure an electrical variable, such as resistance, of a wetness sensor in the absorbent article and to determine whether an incontinence event has occurred and other characteristics of incontinence events which are occurring or have occurred. Such systems may be adapted to alert a carer to the occurrence of an incontinence event so that the carer may check the article and, if necessary, change the article.

Existing incontinence indicators and detection systems are characterised by high costs. Each wetness sensor provided in an absorbent article can cost in the order of several dollars and they are usually designed to be disposed of when the absorbent article is changed. The high cost of consumables means that existing detection systems are typically only used in aged care facilities during an assessment phase. This is where a new subject in an aged care facility has their incontinence assessed during a relatively short period, such as about 72 hours. A schedule for toileting and changing of absorbent articles for the subject is determined by the outcome of this assessment. The relatively short period during which the assessment is conducted means that there is a risk that the subject's incontinence may not be correctly characterised or the characteristics of their incontinence may change over time. Additionally, there are subjects where the reliable application of an incontinence care schedule may prove difficult to implement, such as for those who have limited or no mobility or suffer from significant cognitive impairment.

As such, existing incontinence indicators are not truly used as full-time incontinence indicators or alert systems. Also, the problem of subjects in aged care facilities experiencing less than ideal toileting and absorbent article changing has not truly been solved. Furthermore, in facilities where incontinence indicators and detection systems are deployed it is still common for carers to make manual checks of absorbent articles to verify the accuracy of the assessment and the toileting and changing schedule that has been determined subjects in the care of the facility.

Accordingly, a reliable and cost effective means for full-time detection of incontinence events, including urinary or faecal incontinence events, in an incontinence garment, pad, diaper, or the like worn by a subject is desirable.

Furthermore, it is desirable that such an incontinence detection system be capable of determining urinary incontinence event and associated event volumes and/or the cumulative volume of a sequence of incontinence events to determine when it is appropriate to change an absorbent article.

The discussion of the background to the invention included herein including reference to documents, acts, materials, devices, articles and the like is included to explain the context of the present invention. This is not to be taken as an admission or a suggestion that any of the material referred to was published, known or part of the common general knowledge in any country as at the priority date of any of the claims

SUMMARY OF THE INVENTION

In one aspect, the invention provides an incontinence monitoring system, the system including: a plurality of electrodes on an absorbent article including an absorbent core; a device for electrical connection with the electrodes and monitoring one or more electrical properties of the electrodes, wherein a first set of the electrodes are adapted for detection of wetness associated with urinary incontinence events, and a second set of the electrodes are adapted for detection of faecal incontinence events.

As will become apparent from the foregoing, preferred embodiments of the system comprise resistive sensors and capacitive sensors embedded in an absorbent article, such as diapers for adults or children, and obtaining incontinence data therefrom, namely data indicative of a change in resistance and a change in capacitance of the sensors which is indicative of a faecal incontinence event or a urinary incontinence event. In embodiments, the system is adapted to determine a cumulative measurement of fluid volume in the absorbent article and also the time at which fluid has entered the absorbent article. In some embodiments, the system is adapted to provide a rapid and easily understood indication to a carer of the occurrence of a faecal or urinary incontinence event or that it is necessary to change the absorbent article (e.g. diaper) based on a set of predetermined thresholds. In other embodiments the data can be stored in the device coupled to the sensors. The data may then be sent to an external storage device or a cloud based server to form chronological physiological incontinence data that can be processed either automatically or interactively with a caregiver/clinician, to provide care recommendations, particularly with respect to an incontinence management plan including a schedule of times at which diapers should be changed, volume of fluid to manage between changes and time for toileting.

Preferably, the first set of the electrodes exhibit a change in capacitance upon the ingress of fluid from urinary incontinence events.

Preferably, the first set of the electrodes are comprised of at least two mutually separated flexible conductive electrodes disposed on an outer surface of a water impermeable layer of the absorbent article facing away from the wearer with the absorbent core located on an opposite side of the water impermeable layer facing towards the wearer.

Preferably, the second set of electrodes are adapted to exhibit a change in capacitance or resistance or impedance in the presence of constituents of a faecal incontinence event.

Preferably, the second set of electrodes are comprised of at least two flexible conductive electrodes disposed on a surface of a flexible substrate, wherein the second set of electrodes are located on or towards an inner, body facing water permeable layer wherein the second set of electrodes are adapted to exhibit a change in capacitance or resistance or impedance in the presence of constituents of a faecal incontinence event.

Preferably, each individual electrode is adapted for electrical connection with an individual electrical contact of the device for monitoring an electrical property of the electrodes.

Preferably, the electrodes each include a contact portion adapted for electrical connection with an individual electrical contact of the device, wherein the contact portions of the electrodes are positioned to not overlap with each other.

Preferably each set of sensors are designed for continuous application to rolls of flexible substrate materials, using methods such as rotogravure or flexographic printing of conductive inks to print and cure electrodes directly onto flexible substrates at relatively high speed.

Preferably, the device includes a plurality of electrical contacts each adapted for electrical connection with an individual electrode in the absorbent article.

Preferably, at least some of the electrical contacts of the device are adapted to engage the electrodes from one direction and are positioned adjacent to each other in a transverse direction and not overlapping in a longitudinal direction of the electrodes.

Preferably, the device includes first and second sets of electrical contacts that are adapted to engage from opposite sides of the first and second sets of electrodes disposed on opposite surfaces of the absorbent article.

Preferably, the first and second sets of electrical contacts are disposed on opposing surfaces of a housing of the device adapted to receive and clamp down on the absorbent article and the first and second sets of electrodes therebetween.

Preferably, relative to a longitudinal direction of the electrodes each of the electrical contacts of the first and second sets are positioned adjacent to each other in the transverse direction so as not to overlap in the longitudinal direction with any of the other electrical contacts in the same set.

Preferably, the electrical contacts located consecutively in the transverse direction alternate between electrodes of the first and second sets.

Preferably, the absorbent article includes: a water permeable cover sheet facing towards the wearer; a water impermeable backing sheet facing away from the wearer; an absorbent core positioned between the cover sheet and the backing sheet; the first set of the electrodes being located on a surface of the water impermeable backing sheet with the absorbent core on an opposite side of the backing sheet; and the second set of electrodes being located on or near the water permeable cover sheet.

Preferably, the water impermeable backing sheet is substantially gas impermeable and the first set of electrodes are laid directly on the surface of the backing sheet with the absorbent core on an opposite side of the backing sheet.

Preferably, the water impermeable backing sheet is substantially gas permeable and the first set of electrodes are laid on a water and gas impermeable substrate that is adhered to the surface of the backing sheet with the absorbent core on an opposite side of the backing sheet.

Preferably, a non-woven outer sheet covers the first set of the electrodes and the surface of the water impermeable backing sheet.

Preferably, the second set of electrodes are laid on an at least partially water impermeable substrate that is adhered to an inner surface of the water permeable cover sheet with the absorbent core on an opposite side of the cover sheet.

Preferably, the second set of electrodes are at least partially covered by a faecal sensitive material that breaks down in the presence of a constituent of faecal matter.

Preferably, the faecal sensitive material includes a material that breaks down in the presence of a faecal enzyme such as a lipase or protease.

Preferably, the device further includes an accelerometer adapted for sensing movement of a wearer of the absorbent article to which the device is attached.

Preferably, the device further includes a thermistor adapted for sensing temperature.

Preferably, the device further includes a memory and a processor to store and process data.

Preferably, the device further includes a transmitter adapted to transmit data wirelessly to a receiver.

Preferably, the transmitter is configured to transmit data via the Bluetooth standard.

Preferably, the device is adapted to transmit unique device identity information, sensor data inclusive of absorbent article sensor data, accelerometer data and temperature data, time, and non-sensor status data including battery condition and whether the device is attached or otherwise to one or more sensors.

Preferably, the system further includes a receiver comprised of a remotely located device configured to receive data via the Bluetooth standard, wherein the device is configured to transmit data that can be received by the device without requiring the transmitting device and the receiving device to be paired.

Preferably, the transmitting device is configured to transmit encrypted data and the receiving device is configured to receive and decrypt the data.

Preferably, the receiving device is configured to process the data to determine a wetness state or soiled state of the absorbent article and to provide an alert signalling that the absorbent article requires changing.

Preferably, the device is configured to process a combination of time based sensor data to determine the status of an absorbent article, wherein the status includes wetness or soiling, or an alert condition, and to transmit information indicative of the status or the alert condition to one or more receiving devices.

Preferably, the sensor data and associated sampling time, either in real time or elapsed time, is stored in the device connected to the electrodes and is transmitted to another data storage location where the data related to a particular subject is additively stored.

Preferably, the device is configured for relatively low frequency data sampling wherein the device monitors the electrical property of the sensor in the order of seconds.

Preferably, the device is configured for variable frequency data sampling. In an embodiment, the sampling frequency of a resistance based sensor increases if the device determines that the electrical property of the resistance based sensor or data derived therefrom changes when compared to a trend, or changes when compared to previous data, or when an electrical property changes more than a threshold. In an embodiment the resistance based sensor does not collect any data unless the device determines from the electrical property of the resistance based sensor a change, which thereby causes the device to activate (i.e. wake up) and to collect data. In another embodiment, the wake stage continues for a period of time or until the change in sensor data from the resistance based sensor follows a trend or becomes marginal.

In another aspect, the invention provides an incontinence monitoring sensor for an absorbent article including an absorbent core, the sensor including: a plurality of electrodes adapted for electrical connection with a device for monitoring an electrical property of the electrodes, wherein a first set of the electrodes are adapted for detection of wetness associated with urinary incontinence events, and a second set of the electrodes are adapted for detection of faecal incontinence events.

Preferably, the first set of the electrodes exhibit a change in capacitance upon the ingress of fluid from urinary incontinence events.

Preferably, the first set of the electrodes are comprised of at least two mutually separated flexible conductive electrodes adapted to be disposed on an outer surface of a water impermeable layer of the absorbent article with the absorbent core located on an opposite side of the water impermeable layer.

Preferably, the second set of electrodes are adapted to exhibit a change in capacitance or resistance or impedance in the presence of constituents of a faecal incontinence event.

Preferably, the second set of electrodes are comprised of at least two flexible conductive electrodes disposed on a surface of an at least partially water impermeable flexible substrate, wherein the second set of electrodes are located on or towards an inner water permeable layer or within the absorbent core wherein the second set of electrodes are adapted to exhibit a change in capacitance or resistance or impedance in the presence of constituents of a faecal incontinence event.

Preferably, each individual electrode is adapted for electrical connection with an individual electrical contact of a device for monitoring an electrical property of the electrodes.

Preferably, the electrodes each include a contact portion adapted for electrical connection with an individual electrical contact of the device, wherein the contact portions of the electrodes are positioned to not overlap with each other.

In another aspect, the invention provides a device for electrical connection with a plurality of electrodes of an incontinence monitoring sensor for an absorbent article including an absorbent core, the device including: a housing including a plurality of electrical contacts adapted for electrical connection with a plurality of electrodes of an incontinence monitoring sensor; the device being adapted to monitor an electrical property of the electrodes, wherein a first set of the electrodes are adapted for detection of wetness associated with a urinary incontinence event, and a second set of the electrodes are adapted for detection of a faecal incontinence event.

Preferably, each individual electrical contact is adapted for electrical connection with an individual electrode of the sensor.

Preferably, the electrodes each include a contact portion adapted for electrical connection with an individual electrical contact of the device, wherein the contact portions of the electrodes are positioned to not overlap with each other.

Preferably, at least some of the electrical contacts are adapted to engage the electrodes from one direction and are positioned adjacent to each other in a transverse direction and not overlapping in a longitudinal direction of the electrodes.

Preferably, the device includes first and second sets of electrical contacts that are adapted to engage from opposite sides of the first and second sets of electrodes disposed on opposite surfaces of an absorbent article.

Preferably, the first and second sets of electrical contacts are disposed on opposing surfaces of the housing adapted to receive and clamp down on the absorbent article and the first and second sets of electrodes therebetween.

Preferably, the electrical contacts located consecutively in the transverse direction alternate between electrodes of the first and second sets.

Preferably, the device is adapted to detect a change in capacitance of at least some of the electrodes associated with a urinary incontinence event and to detect a change in resistance of at least some of the electrodes associated with a faecal incontinence event.

Preferably, the device further includes an accelerometer adapted for sensing movement of a wearer of the absorbent article to which the device is attached.

Preferably, the device further includes a thermistor adapted for sensing temperature.

Preferably, the device further includes a transmitter adapted to transmit data wirelessly to a receiver, preferably via the Bluetooth standard.

In another aspect, the invention includes an absorbent article adapted for detection of urinary and faecal incontinence events, the pad including: a water permeable cover sheet; a water impermeable backing sheet; an absorbent core positioned between the cover sheet and the backing sheet; a first set of electrodes located on a surface of the water impermeable backing sheet with the absorbent core on an opposite side of the backing sheet; and a second set of electrodes located on or near the water permeable cover sheet.

Preferably, the first set of electrodes are laid on a substrate that is adhered to the surface of the water impermeable backing sheet with the absorbent core on an opposite side of the backing sheet.

Preferably, a non-woven outer sheet covers the first set of the electrodes and the surface of the water impermeable backing sheet on the opposite side to the absorbent core.

Preferably, the second set of electrodes are laid on an at least partially impermeable substrate that is adhered to a surface of the water permeable cover sheet with the absorbent core on an opposite side of the cover sheet.

Preferably, the second set of electrodes are covered by a faecal sensitive material that breaks down in the presence of a constituent of faecal matter.

Preferably, the faecal sensitive material includes a material that breaks down in the presence of a faecal enzyme such as a lipase or protease.

Preferably, the first set of electrodes are adapted for detection of wetness associated with a urinary incontinence event by exhibiting a change in capacitance and the second set of electrodes are adapted for detection of a faecal incontinence event by exhibiting a change in resistance.

In yet another aspect, the invention provides a method for monitoring incontinence including: electrically connecting a device to electrodes applied to an absorbent pad worn by a subject; monitoring an electrical property exhibited by the electrodes; detecting a change in the electrical property due to the presence of fluid from a urinary incontinence event or constituents of a faecal incontinence event in the absorbent pad; determining from the change in the electrical property the occurrence of a urinary or faecal incontinence event; processing data representative of the change in one or more of the electrical properties to determine if a faecal incontinence event has occurred in the absorbent article or that cumulative urinary events have reached or are expected to reach a threshold; and providing an alert indicating that the absorbent article requires changing.

Preferably, processing data representative of the change in one or more of the electrical properties includes applying a function to the data based on factors including: i) the quantity of liquid in the absorbent article; ii) the electrical properties of the electrodes that change in the presence of fluid from urinary events; and iii) accelerometer data from the device representative of movement and/or pressure.

Preferably, the method includes time stamping and storing sets of the data and executing a function on the time stamped data to determine a model for predicting when a pre-defined wetness threshold will be reached due to cumulative urinary events occurring in an absorbent article and causing a device to provide an alert indicating either: i) the future time when the pre-defined threshold will be reached; or ii) that a pre-defined time interval for changing the absorbent article has been reached, wherein the interval is determined as an off-set from the future time when the pre-defined threshold will be reached.

Preferably, the method includes detecting a change in capacitance of at least some of the electrodes to determine the presence of fluid from a urinary incontinence event and detecting a change in resistance or capacitance or impedance of at least some of the electrodes to determine the presence or constituents of a faecal incontinence event.

In an embodiment, the device is configured for a fixed sampling frequency for the second set of electrodes located on or towards an inner water permeable layer. In another embodiment the device is configured for a variable sampling frequency for the second set of electrodes located on or towards an inner water permeable layer. The sampling frequency changes depending on any one or more of: the time of the day, historical incontinence data related to the subject, time since the last incontinence event, time since last toileting, a size of the last incontinence event, and a change in electrical properties. For example, the sampling frequency may increase when there is a change in electrical behaviour of the electrodes detected by the device that is greater than a threshold or there is a change in a trend of the data derived from the electrical behaviour. In some embodiments comprising sensors located at or towards the inner layer, where capacitance is also being monitored, the device is configured for a moderately low frequency sampling rate of data wherein the device monitors the electrical property of the sensor every 1 to 90 seconds. On the other hand, in embodiments comprising sensors located at or towards the inner layer, where resistances or impedance is being monitored, the frequency or sampling rate is more frequent, such as in the order of seconds or fractions of a second.

Fluid from incontinence events will contain water and other chemicals excreted by the body. In the case of urine, the fluid will contain water and ammonium, sulphate, phosphate, sodium, chloride and potassium and in the case of faecal matter, the fluid will contain water and many organic and inorganic compounds, fatty acids, sulfur and nitrogen containing compounds. Accordingly, in embodiments of the invention, the electrodes are adapted to exhibit a change in electrical property in the presence of fluids present in urine and faecal incontinence events as well as fluids that may be contained in other bodily excretions or discharges.

Embodiments of the invention are advantageous in that because they can provide a system, a device, an absorbent article and sensor combination and a method adapted for daily use. Embodiments of the invention can provide a platform solution designed to allow additional sensor technology and/or data analysis to deliver care benefits to users that are in addition to and supplement incontinence monitoring and management outcomes.

BRIEF DESCRIPTION OF DRAWINGS

The present invention will now be described in more detail with reference to embodiments of the invention illustrated in the figures, wherein.

DETAILED DESCRIPTION

Figure 1A:
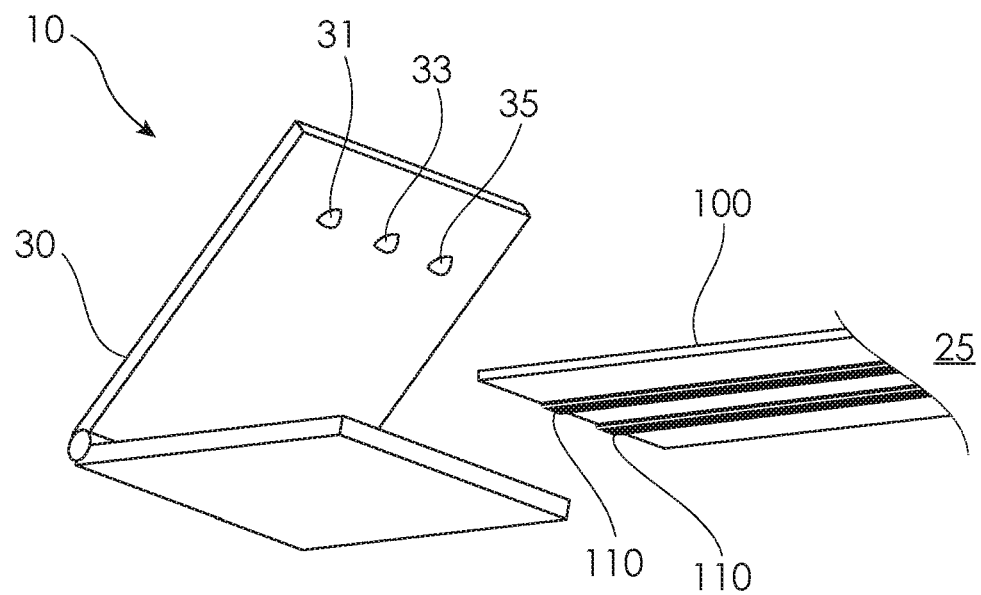
FIGS. 1a and 1b illustrate below and above perspective views of an incontinence monitoring system in accordance with an embodiment of the invention comprising a plurality of electrodes of a sensor for an absorbent article and a device for electrical connection with the electrodes for monitoring one or more electrical properties of the electrodes.
Figure 1B:
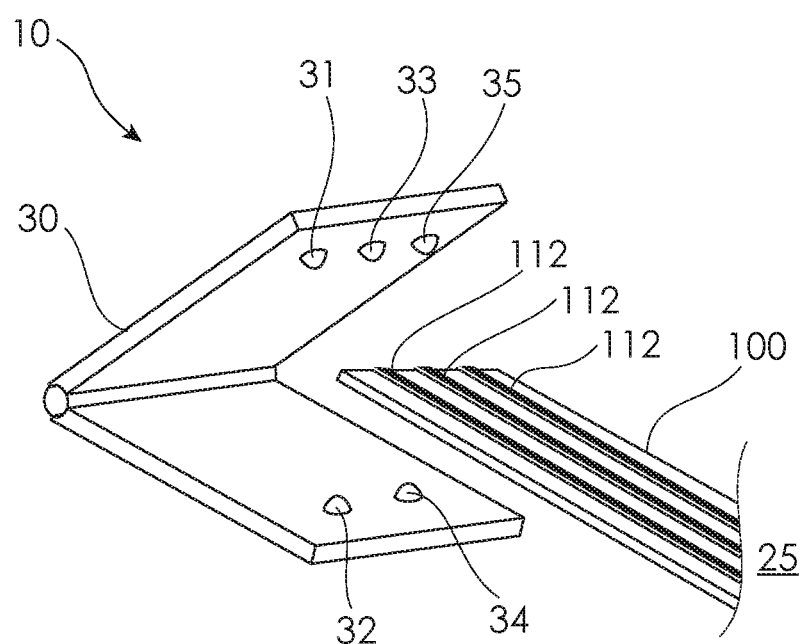

In one aspect, and with reference to FIGS. 1a, 1b, 2a, 2b and 3, the invention relates to an incontinence monitoring system 10 including a plurality of electrodes 110, 112 on an absorbent article 25 including an absorbent core 27, a device 30 for electrical connection with the electrodes 110, 112 and monitoring an electrical property of the electrodes 110, 112. A first set of the electrodes 112 are adapted for detection of wetness associated with a urinary incontinence event, and a second set of the electrodes 110 are adapted for detection of a faecal incontinence event.

The plurality of electrodes 110, 112 form part of an incontinence sensor 100 that is formed in the absorbent article 25 during manufacture. As discussed below and as illustrated in FIGS. 5, 6 and 7, the system 10 is adapted so that the device 40, which is attached to the sensor 100 embedded in the absorbent article 25 and worn by a subject, transmits data to another device, such as a smartphone 45 or a tablet or a fixed device (e.g. Room Monitor) 46, or a smartwatch 47, to communicate incontinence related information about the subject.

Figure 5:
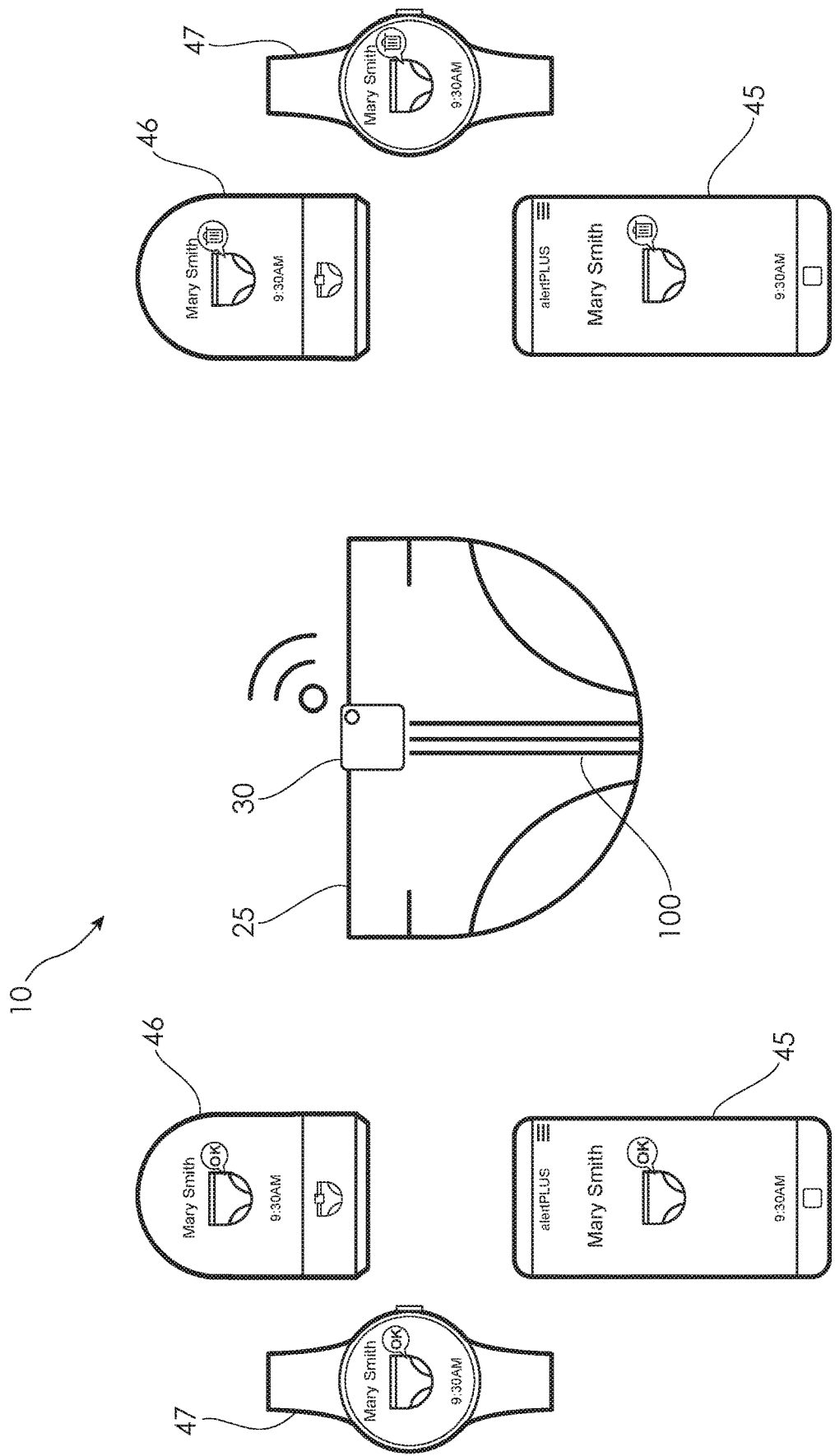
FIG. 5 illustrates a schematic view of the incontinence detection system of FIG. 1 illustrating the sensor and diaper coupled to the device that is adapted to monitor the electrical behaviour of the electrodes and to transmit signals directly to a remote device such as a smartphone, a smartwatch or a fixed device or room monitor such as via a wireless data transmission protocol such as Bluetooth, wherein in one instance the devices are displaying that the absorbent article doesn't require changing whereas in the other instance the devices are indicating or providing an alert that the absorbent article requires changing.
Figure 6:
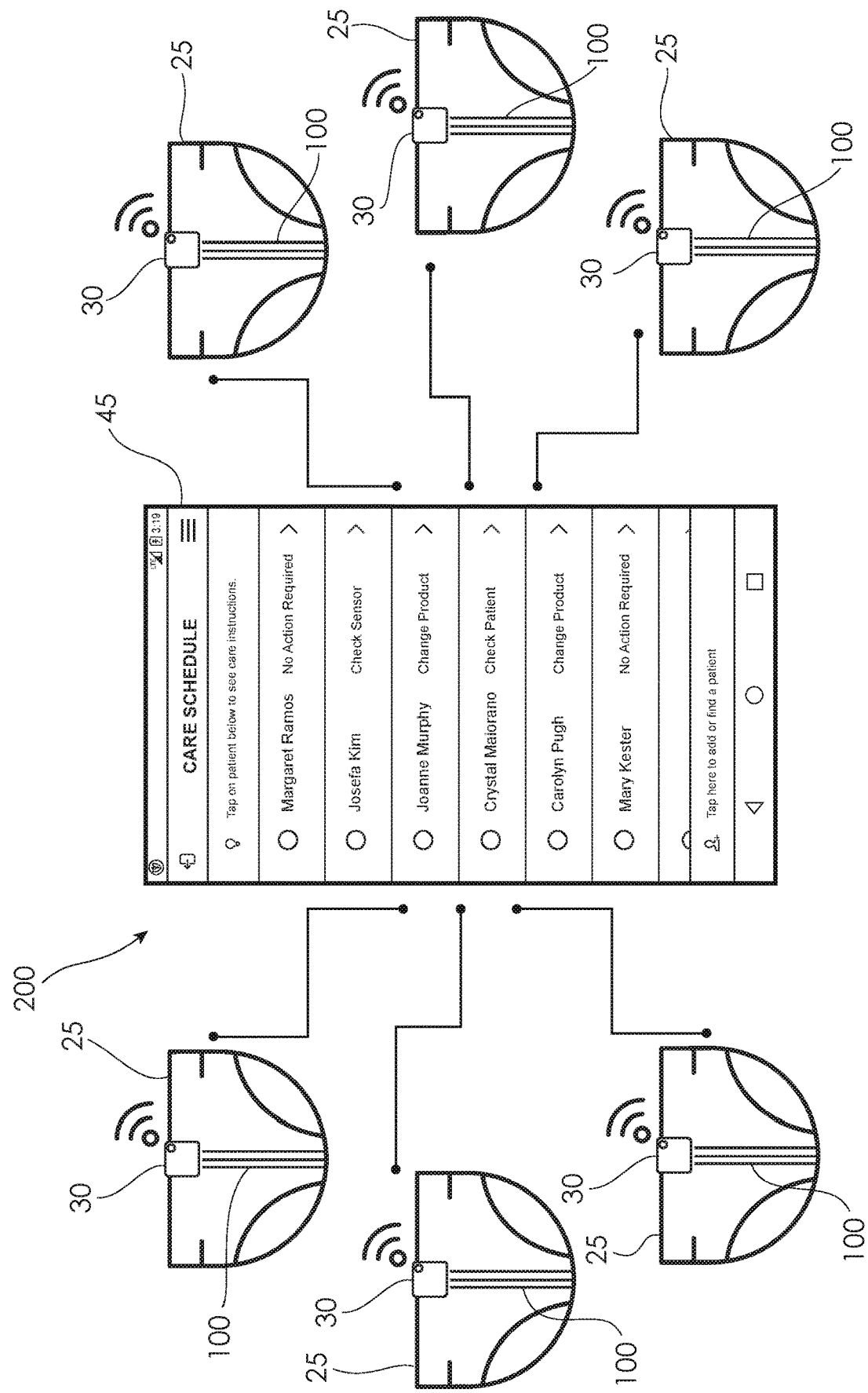
FIG. 6 illustrates a schematic view of a number of sensor, diaper and device combinations and a single remote device such as a smartphone, a smartwatch or a fixed device or room monitor such as via a wireless data transmission protocol such as Bluetooth where the device is displaying that some of the absorbent articles require changing and some do not require changing.
Figure 7:
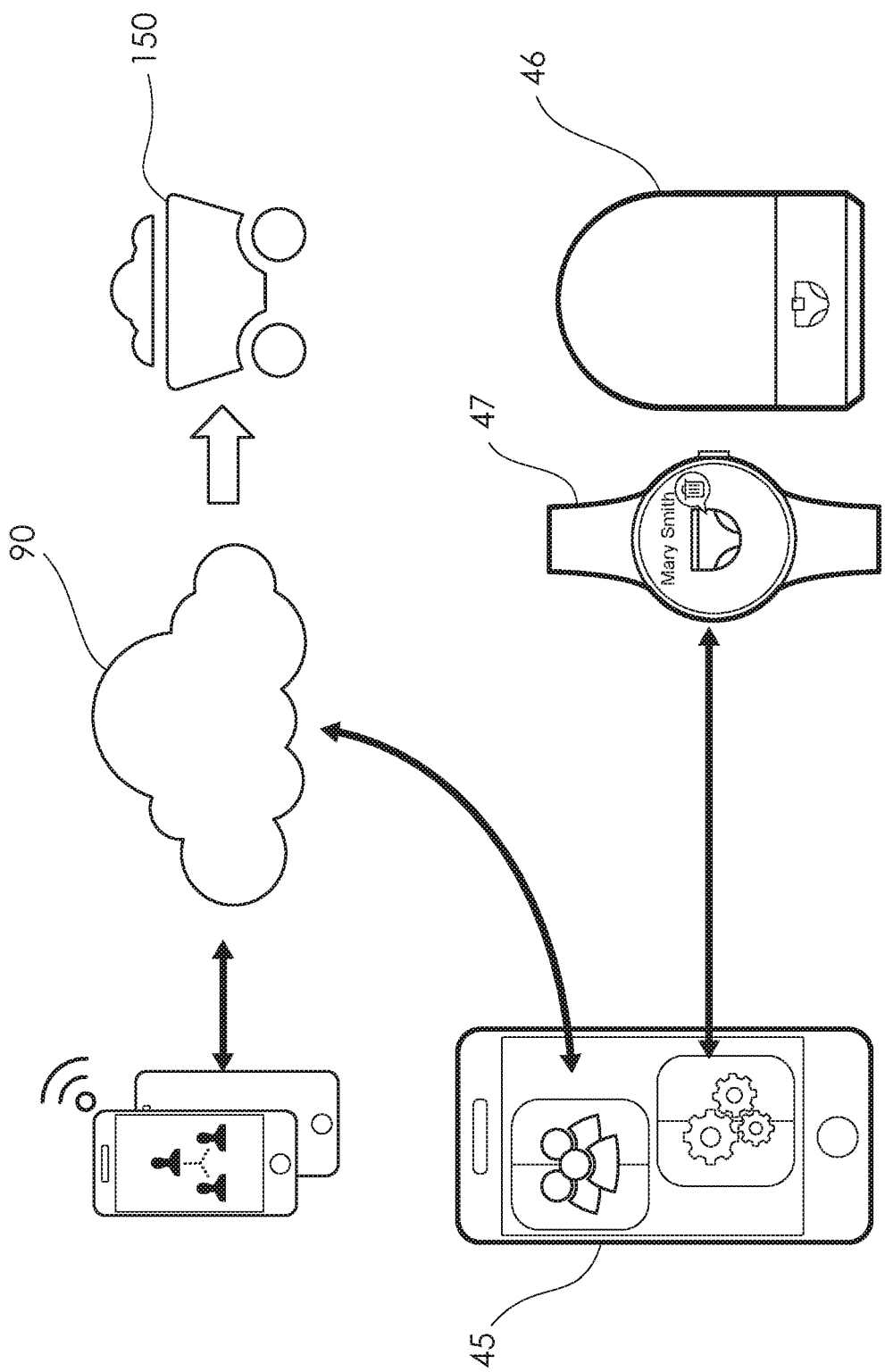
FIG. 7 illustrates a schematic view of a system including remote devices including a smartwatch and a fixed device or room monitor transmitting and receiving data wirelessly with another remote device in the form of a smartphone which in turn is transmitting and receiving data to a cloud based server that is adapted to process data received from the smartphone associated with one or more users of the platform in one location and to transmit and receive data with one or more users in other settings, wherein the cloud based server is configured to generate data useful for other external purposes (e.g. for information for payers, inventory management, regulatory compliance)

Another example of the architecture is the sensor network 200 illustrated in FIG. 6 where a plurality of the devices 30 connected to respective absorbent articles 25 are adapted to relay data to a single device such as a smartphone 45, as illustrated in FIG. 5, or a fixed device 46 or smartwatch 47.

The system 10 is adapted for use as a full-time wetness event detection system for such as for use in an environment, such as a hospital or aged care facility. The system 10 generates and processes data to determine quantitative and/or qualitative information about a subject wearing the absorbent article 25 and device 30 combination and their incontinence such as the presence of wetness and/or faecal matter in the absorbent article 25 and/or the time of the urinary or faecal incontinence event and/or a quantitative measure such as a volume of wetness associated with an individual urinary incontinence event and/or a cumulative volume of a sequence of wetness events and/or data indicative of one or more trends. The system 10 may also be configured to set one or more objectives such as a threshold of wetness the absorbent article 25 can hold before leakage occurs, or before a patient's skin that is contained within the absorbent article 25 is exposed to prolonged wetness and providing an alert to a carer to change the article 25. The system 10 may be set with a conservative threshold for subjects at higher risk to an adverse skin integrity event. The system 10 may also be configured to make predictions about when the next wetness event may occur in respect of individual subjects or when the absorbent article may reach a future alert state and provide alerts to a carer a predetermined time before the expected occurrence of the wetness event or the future alert state.

The device 30 is adapted to collect data, based on the electrical behaviour of conductive electrodes comprising the sensor 100 in the absorbent article 25 such as capacitance and/or resistance, indicative of a cumulative measurement of fluid volume in the absorbent article and also the time at which fluid has entered the absorbent article 25 and/or indicative of the presence of constituents of faecal matter in the absorbent article 25. This data is initially stored in the device 30 coupled to the sensor 100. As illustrated in FIG. 7, the data may then be sent by the device 30 to an external storage device such as to a remote server 90 to form chronological physiological incontinence data (i.e. historical incontinence data) that can be processed either automatically or interactively with a caregiver/clinician, to provide care recommendations, particularly with respect to an incontinence management plan or schedule including time to change, time for toileting and the like. The data may also be processed directly on the device, to determine the status of wetness or soiling of an absorbent article, or that an alert condition has been reached, and to then send that data to one or more receivers for storage and further processing or for alerting purposes.

Figure 2A:
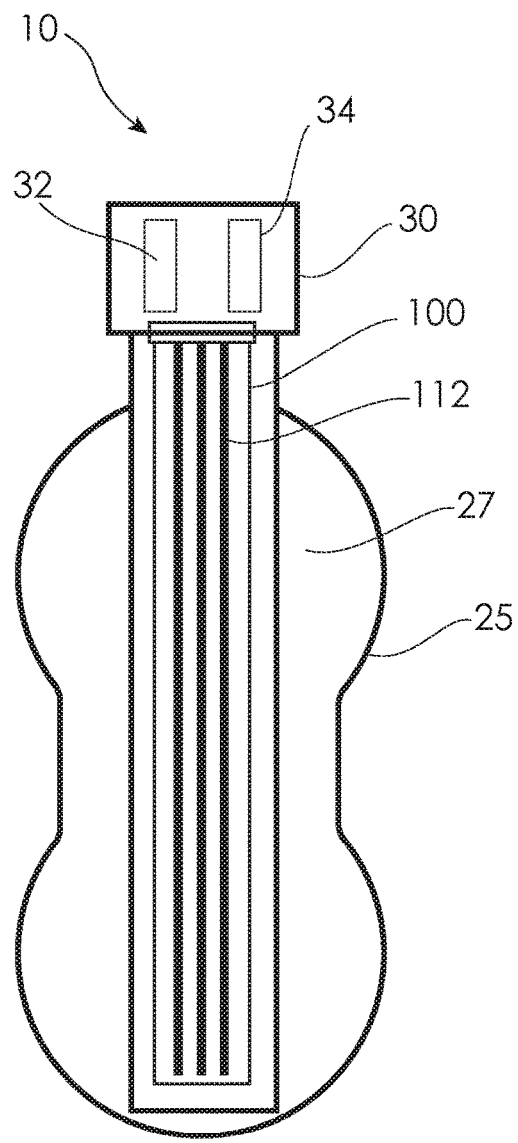
FIGS. 2a and 2b illustrate plan views of the outer surface of an absorbent article (e.g. a diaper) facing away from the wearer's body and an inner surface of the absorbent article facing towards the wearer's body and showing the plurality incontinence sensor comprising a first and a second set of electrodes applied to the absorbent article and electrically coupled to the device for monitoring the electrical properties of the electrodes.
Figure 2B:
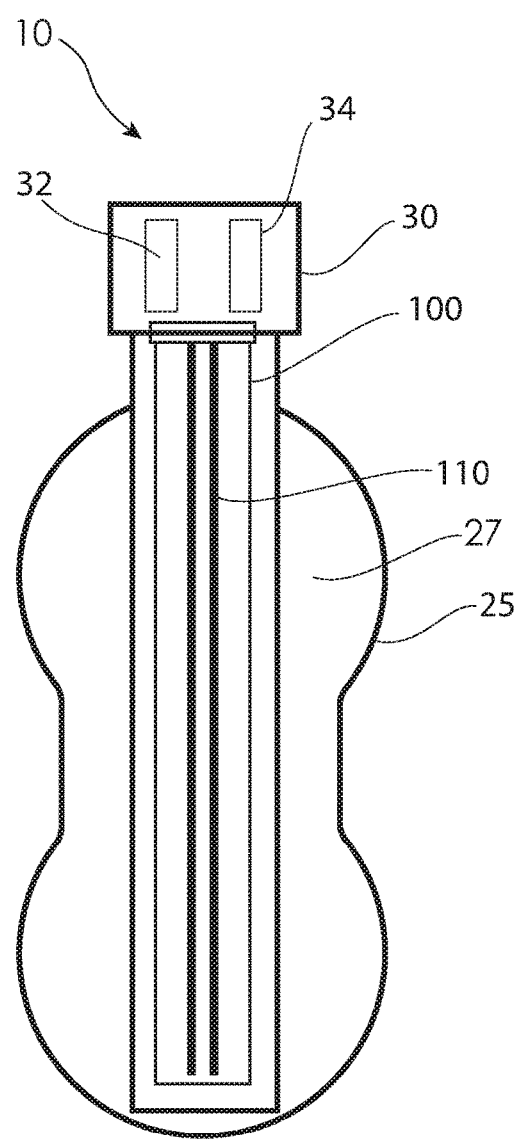

FIGS. 1a, 1b, 2a and 2b illustrate an incontinence detection sensor 100 incorporated in an absorbent article 25 in accordance with an embodiment of the present invention. FIG. 2a illustrates one side (the outer side facing away from the wearer) of the sensor 100 and absorbent article 25 and FIG. 2b illustrates the reverse side (the inner side facing towards the wearer). The sensor 100 includes a plurality of electrodes 110, 112 that are each preferably comprised of a printed electrically conductive material. The electrodes may be formed out of printable inks or pastes, including carbon, silver or graphene, or a blended formulation containing these and/or other chemicals required to achieve an appropriate printing viscosity and sheet resistance. The sensors are configured to form continuous and symmetrical patterns that then enable continuous manufacture of the sensor and associated incontinence articles using existing manufacturing processes without any significant modification to those processes.

The electrodes 110, 112 of the sensor 100 exhibit electrical properties that change in the presence of wetness associated with a urinary incontinence event or in the presence of constituents of faecal matter associated with a faecal incontinence event. In embodiments, the electrical property may be electrical resistance, capacitance or voltage.

Figure 3:
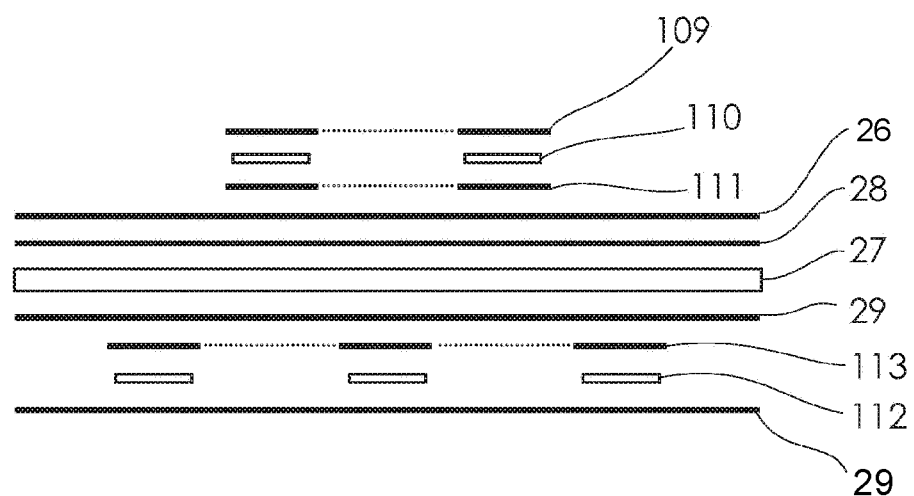
FIG. 3 illustrates an end view of a transverse cross section of an embodiment of the sensor and absorbent article combination of FIGS. 2a and 2b comprising a first set of electrodes on an outer surface of a water impermeable layer facing away from the wearer and a second set of electrodes on an inner surface of a water permeable layer facing towards the wearer.

In embodiments, and as shown in FIGS. 2a, 2b and 3, the sensor 100 is comprised of a first set of at least two mutually separated and flexible conductive electrodes 110 disposed on a surface of a flexible substrate 111. The first set of electrodes 110 are adapted for detection of a faecal incontinence event in a manner described herein. The substrate 111 may be water impermeable or water permeable and is applied to the inner water permeable layer 26 of an absorbent article 25 such as a diaper. The substrate 111 may be designed to be as wide as the water permeable layer 26, or may be designed to be as wide as, or a little wider than, the conductive electrodes 110, either individually or collectively. The electrodes 110 may alternatively be applied to the inner (wearer facing) surface or the outer surface (i.e. the surface facing away from the wearer) of the inner water permeable layer 26. The electrodes 110 may be applied directly to the inner water permeable layer 26 without any intervening substrate. The electrodes 110 may be encapsulated in an insulating material, for example if the electrical property being monitored is capacitance. Otherwise, the electrodes 110 may be exposed to the surrounding environment and any wetness resulting from a urinary or faecal voiding event, if resistance is the electrical property being monitored.

Preferably, the electrodes 110 are covered by a faeces-sensitive material 109. Preferably, the faeces-sensitive material 109 covering, at least in part, the electrodes 110 is a material that reacts to the presence of a faecal lipase or protease. In embodiments, the faeces-sensitive material 109 covering, at least in part, the conductive element includes a lipid, preferably a triglyceride. The faeces-sensitive material 109 covering, at least in part, the conductive element can include tristearin (glyceryl tristearate, 1,3-di(octadecanoyloxy)propan-2-yl octadecanoate). In embodiments, the faeces-sensitive material 109 covering, at least in part, the conductive element is a combination of tristearin and stearic acid.

The faeces sensitive material 109 is comprised of material that breaks-down in the presence of constituents of faecal matter. Where the faeces sensitive material 109 is comprised of a lipid a chemical reaction with a faecal enzyme such as a faecal lipase or protease breaks-down the layer which allows the ingress of liquid or other material into the faeces sensitive layer to approach or come into contact with one or more of the electrodes. While the faeces-sensitive material 109 covering, at least in part, the conductive elements 110 remains intact it acts as an insulator to electrically insulate and/or chemically insulate the conductive elements 110 from each other. However, with the break-down of the faeces-sensitive material 109 covering faecal matter or liquid is allowed to ingress between the electrodes 110. The electrical property exhibited by the electrodes 110, such as resistance between the electrodes 110, changes following the reaction of the preferably organic faeces-sensitive material 109 which is detected by the device 30. The change in the electrical property of the first set of electrodes 110 detected by the device 30 can be a difference in the resistance between the electrodes 110 when the preferably organic faeces-sensitive material is between the electrodes and when the reaction of the preferably organic faeces-sensitive material allows ingress of faecal or other matter between the electrodes 110. In another embodiment, the change in the electrical property of the first set of electrodes 110 detected by the device 30 can be a change in capacitance or voltage between the electrodes 110.

The electrodes 110 themselves may be formed of a faeces sensitive material such as silver or a silver alloy which again will exhibit a change in electrical property, namely resistance, in the presence of faecal matter.

Beneath the water permeable layer 26 is a layer of absorbent material 27 that is adapted to absorb wetness such as urine or constituents of faecal matter. Between the water permeable layer 26 and the layer of absorbent material 27 is an acquisition layer 28 comprised of a material adapted to distribute liquid that penetrates the water permeable layer 26 across the absorbent layer 27 to ameliorate the concentration of liquid in a particular location in the absorbent layer 27. An outer water impermeable layer 29 is applied to the opposite side of the layer of absorbent material 27 facing away from the wearer. In another form, the electrodes 110 and associated substrate 111 and faecal sensitive material 109 may alternatively be applied to the inner surface of the absorbent layer or core 29 or to the top or bottom surface of the water permeable layer 26.

In addition to the first set of the electrodes 110, the sensor 100 includes a second set of the electrodes 112. The second set of the electrodes 112 include at least two and preferably at least three mutually separated and flexible conductive electrodes 112 disposed on a surface of a preferably water impermeable flexible substrate 113 which in turn is applied to the outer water impermeable layer 29 of the absorbent article 25 (e.g. diaper). The substrate 113 may be water permeable but preferably is water impermeable and is applied to the outer surface of the outer water impermeable layer 29. The electrodes 112 may alternatively be applied directly to the inner surface of the outer water permeable or impermeable layer 29, although in an embodiment where capacitance of the electrodes 112 is being monitored a water impermeable layer should be positioned between the electrodes 112 and the absorbent layer 27. The electrodes 112 may alternatively be applied directly to the outer layer of the absorbent layer or core 27 although again where capacitance of the electrodes 112 is being monitored a water impermeable layer is positioned between the electrodes 112 and the absorbent layer 27.

The electrodes 112 may be encapsulated in an insulating material, if the electrical property being monitored is capacitance, or the electrodes may be exposed to the surrounding environment or wetness in the absorbent layer 27, if the electrical property being monitored is resistance or impedance.

In preferred embodiments, and as illustrated in FIGS. 1, 2a, 2b and 3, the sensor 100 includes both the first and second sets of the electrodes 110, 112 with the first one of the sets 110 located at or near the inner (i.e. wearer facing) water permeable layer 26 and the second set 112 located at or near the outer (i.e. facing away from the wearer) water impermeable layer 29 and preferably on an outer surface thereof so as to be insulated from the absorbent layer or core 27 by the water impermeable outer layer 29. The water impermeable outer layer 29 may be comprised of a gas impermeable layer, as in the case of adult incontinence garments, or gas permeable material as in the case of infant incontinence garments (i.e. diapers), In preferred embodiments, the electrical property to be monitored of the first set of the electrodes 110 located at or towards the inner water permeable layer 26 is resistance, or it may be capacitance or impedance, and the electrical property to be monitored of the second set of electrodes 112 located at or towards the outer water impermeable layer 29 is capacitance.

Figure 4:
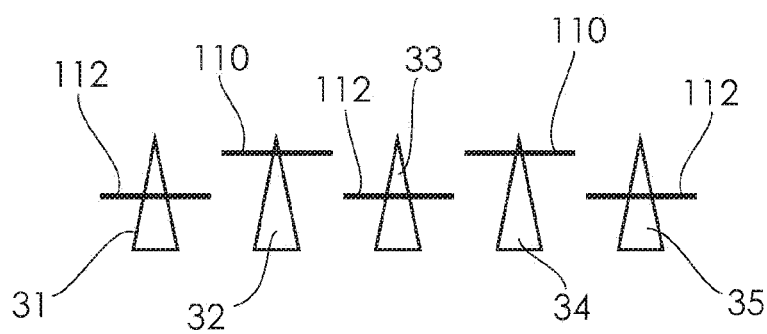
FIG. 4 illustrates a schematic representation of an end view of a transverse cross section of the sensor comprising the first and second sets of electrodes and an array of electrical contacts of the device in the form of prongs adapted to pierce the electrodes of the sensor array and thereby initiate electrical contact with each of the electrodes.
Figure 4A:
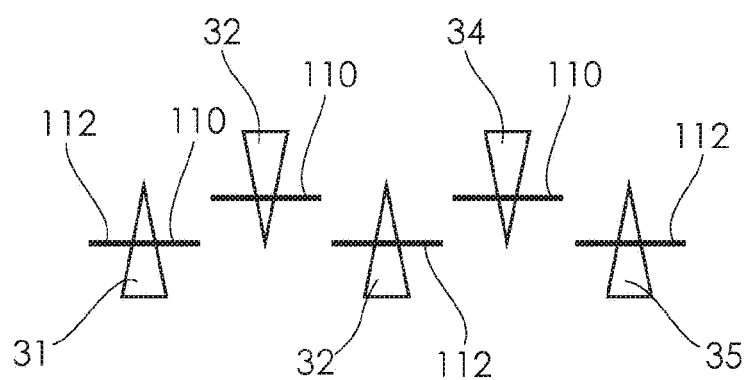
FIG. 4a illustrates a schematic representation of an end view of a transverse cross section of the sensor comprising the first and second sets of electrodes and an array of electrical contacts of the device in the form of prongs adapted to pierce the electrodes of the sensor array, albeit some of the prongs are oriented in one direction and some of the prongs are oriented in an opposite direction.

As can be seen in FIGS. 1 and 2a, 2b, one end of the electrodes 110, 112 are adapted to be engaged by the wearable device 30. As shown in FIGS. 1, 4a and 4b, the device 30 includes a plurality of electrical contact members 31-35 that are formed into prongs. The prong shaped electrical contact members 31-35 are adapted to be forced through respective ones of the electrodes 110, 112 and form an electrical connection therewith. As shown in FIGS. 1 and 3a, 3b, the electrodes 110, 112, or at least a portion of the electrodes 110, 112 for establishing an electrical contact with the contacts 31-35 of the device 30, are each located in a respective transverse location without any overlap such that each one of the prong-shaped electrical contact members 31-35 will penetrate and establish an electrical contact with only a respective one of the electrodes 110, 112. Furthermore, the configuration of the electrodes 110, 112 and the prong shaped electrical contact members 31-35 is such that they are positioned symmetrically about a longitudinal axis such that the sensor 100 and the device 30 may be oriented relative to each other in two ways (i.e. with the device 30 oriented to the front or to the rear relative to subject 20 wearing the sensor 100 and absorbent article 25 combination). The symmetrical positioning of the prong shaped electrical contact members 31-35 and the electrodes 110, 112 means that the contact members 31-35 will establish an electrical connection with the appropriate electrodes 110, 112 regardless of whether the transmitting device 30 is oriented forwards or backwards when connected to the sensor 100.

In another embodiment, device 30 may be configured to utilise a contactless connection with the sensor 100 or with the electrodes 110, 112 thereof.

During use of the sensor 100 in an absorbent article 25, the device 30 is adapted for monitoring one or more electrical properties of the first and second sets of electrodes 110, 112 of the sensor 100 such as the resistance, voltage or capacitance between the electrodes 110, 112. Upon the ingress of water or some other fluid or urine or faecal constituent into the absorbent layer 27, such as with the occurrence of a urinary or faecal incontinence event, changes in the electrical properties of the sensor 100 may be detected by the device 30 as described in the foregoing.

In the case of the first set of the electrodes 110 located at or towards the inner water permeable layer 26, with the occurrence of a faecal incontinence event in the absorbent article 25, constituents of the faecal matter react with the faeces-sensitive material 109 covering and insulating the electrodes 110 from each other to allow ingress of faecal matter or liquid. Thus, the flexible electrodes 110 and the liquid or other constituents of the urine or faecal matter contained in the absorbent layer 27 form a circuit in which the liquid or other urine or faecal constituents in the absorbent layer acts as a resistive conductor. The first set of the flexible electrodes 110 serve as two electrodes of the circuit and the liquid in the absorbent layer 27 serves as an electrolyte (electrolyte solution) in the circuit. The resistance value of the circuit is related to the content and distribution of the liquid or other urine or faecal constituents contained in the absorbent layer 27. The wetness state or soiled state of the absorbent layer 27 of the absorbent article 25 can be obtained by detecting the resistance value of the circuit and analyzing the pattern of changes in the resistance value. In this embodiment, the electrical property exhibited by the sensor 100, or at least the component comprised of the electrodes 110 located towards the inner layer 26 of the absorbent article 25, that principally changes following the ingress of water or other urine or faecal constituents into the absorbent layer 27 is resistance. Over time, as more incontinence events occur, more water or other urine or faecal constituents is absorbed into the absorbent layer 27 and this is detected in a further change in resistance. The resistance value is principally useful in indicating qualitative information such as the occurrence of a faecal incontinence event into the absorbent article 25 and is not as suited to indicate quantitative information such as the amount of liquid in the event or the cumulative amount of liquid present in the absorbent layer or core 27.

In other embodiments, the electrical property, or the change thereof, being measured between the pair of the first set of flexible electrodes 110 located at or near the inner permeable layer 26 may be capacitance. In other embodiments, the electrical property, or a change thereof, being measured between the pair of the first set of electrodes 110 located at or near the inner permeable layer 26 may be resistance, or a change thereof, occurring after the degradation of a faecal sensitive material insulating the first set of the electrodes 110 from each other or from degradation of faecal sensitive electrodes such as electrodes comprised of silver or silver alloy.

In other embodiments, the detection of a faecal event may make use of a change in resonance of a resonance circuit, with the flexible electrodes 110 and the faeces-sensitive material 109 acting as a variable resistive, capacitive or inductive element in a resonant circuit, and with the other elements of the resonant circuit, and measurement, contained within the device 30.

In the case of the second set of electrodes 112, the water impermeable outer layer 29 and/or the substrate 113 or the insulation around the electrodes 112, and the liquid or other urine or faecal constituents contained in the absorbent layer 27 form a non-polar variable electrolytic capacitor. Pairs of the second set of electrodes 112 serve as two electrodes of the electrolytic capacitor, the insulation around the second set electrodes 112 and/or the water impermeable outer layer 29 and/or the substrate 113 serve as a dielectric of the electrolytic capacitor, and the liquid or other urine or faecal constituents in the absorbent layer 27 serves as an electrolyte (electrolyte solution) of the electrolytic capacitor. The capacitance value of the electrolytic capacitor is related to the content and distribution of the liquid or other urine or faecal constituents contained in the absorbent layer 27. The wetness state, or soiled state, of the absorbent layer 27 of the absorbent article 25 can be obtained by detecting the capacitance value, or voltage, of the electrolytic capacitor and analyzing the pattern of changes in the capacitance value. In this embodiment, the electrical property exhibited by the second set of the electrodes 112 located towards the outer layer 29 of the absorbent article 25, that principally changes following the ingress of water or other urine or faecal constituents into the absorbent layer 27 is capacitance or voltage. Over time, as more incontinence events occur, more water or other urine or faecal constituents is absorbed into the absorbent layer 27 and this is detected in a further change in capacitance value or voltage. The capacitance value is useful in indicating qualitative information such as the presence of liquid associated with a urinary incontinence event and also quantitative information such as the volume of liquid in a urinary incontinence event or the cumulative amount of liquid present in the absorbent layer or core 27.

Some absorbent articles 25 are provided with a water impermeable, but breathable or gas permeable, outer layer 29. Examples of this type of construction are typically found in infant diapers as opposed to adult absorbent articles that are typically provided with gas impermeable outer layer 29. Outer layers 29 formed from polyethylene, are permeable to gases and water vapours but impermeable to liquid. It has been found that water vapour permeating through the outer layer 29 could alter the electrical properties of capacitive sensors printed or attached to the outer layer 29. To overcome this issue, a moisture proof barrier (impervious to vapour and liquid), such as the water impermeable substrate layer 113, can be located under the conductive electrodes 112 located at or near the outer layer 29. For example, an impermeable ink may be printed or otherwise provided onto the substrate 113 of the capacitive sensors 112, either slightly wider than each conductive electrode 112 or slightly wider than the complete set of capacitive electrodes 112. The moisture proof ink is cured and then the conductive electrodes 112 are printed or attached on top of the impermeable barrier of the substrate layer 113. Another method is to laminate an impermeable barrier, for example with non-breathable polyethylene, onto a breathable outer layer 29 with the impermeable barrier designed to be slightly wider than the complete configuration of the second set of the electrodes 112.

Figure 8:
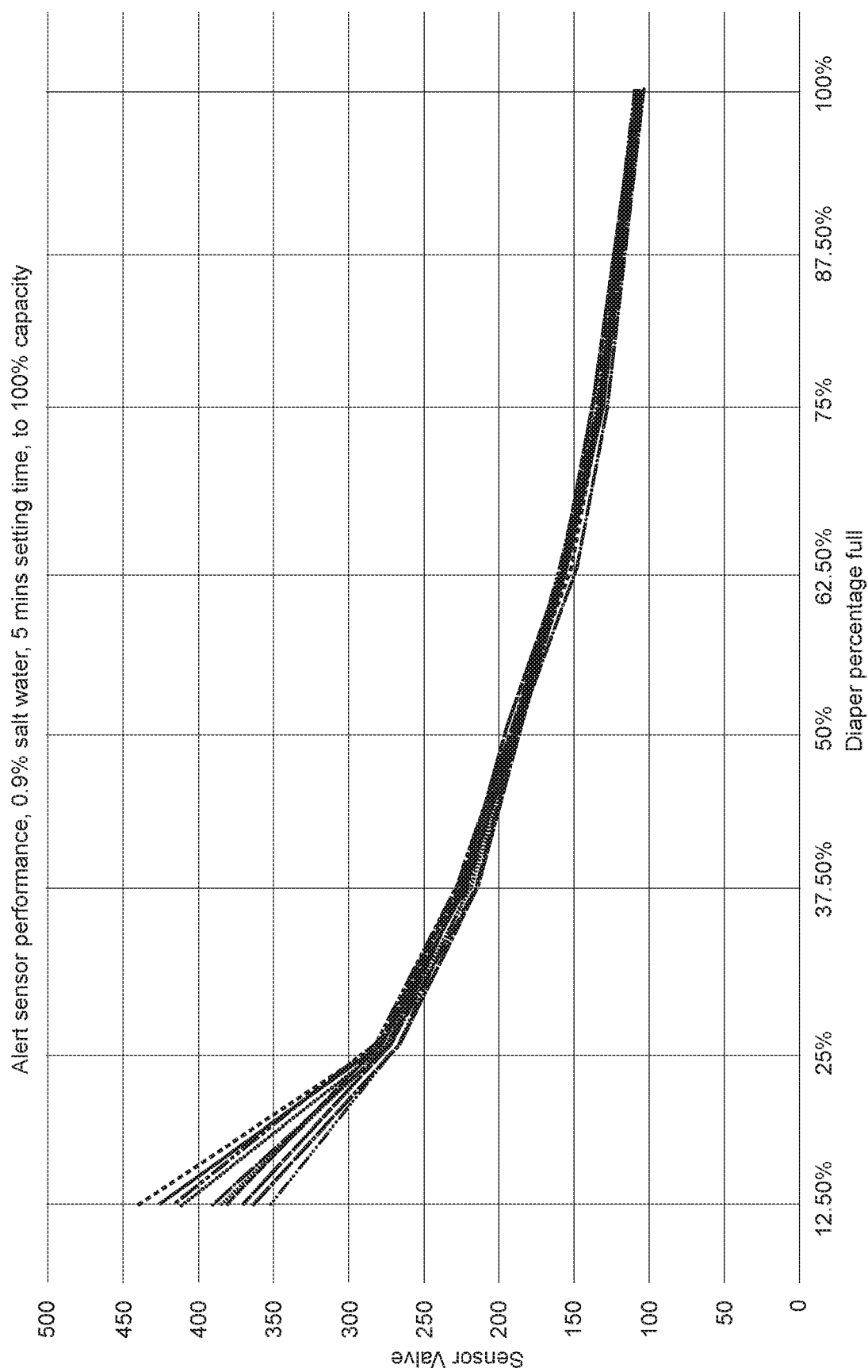
FIG. 8 illustrates a graph of test results of a plurality of diaper and sensor combinations illustrating the response of the sensor to volumes of wetness discharged into each diaper.

FIG. 8 illustrates a graph of test results of a plurality of diaper and sensor combinations illustrating the response of the sensor 100 to volumes of wetness discharged into a diaper. The horizontal axis represents amounts of water discharged into 10 diapers in 122 gram increments where the total capacity of the diapers is 1000 grams. The vertical axis represents the electrical response of the sensor 100 as detected by the device 30 upon the discharge of each 122 gram amount of water into the diapers. The results indicated that the sensor 100 exhibits a good response to each discharge of water into the diapers enabling a relatively accurate determination to be made as to the occurrence of incontinence events in an absorbent article as well as the cumulative volume of the events and thereby make accurate assessments as to the appropriate time to change an absorbent article.

In an embodiment, the electrical response of the sensor 100 as detected by the device 30 represent how much liquid has been received by the absorbent article 25 and how full the absorbent article 25 is. The absorbent article 25 may be of different sizes, shapes and capacities. However, the sensor value is independent of the absorbent article 25 configuration but is, at least to an extent, dependant on the degree of wetness of the absorbent article 25, and in particular the absorbent core 27, relative to its capacity. In another embodiment the system 10 is configured to take into account variables such as the absorbent article 25 type, capacity or size.

In addition to the electrical contact members 31-35, the device 30 includes a processor 32, a power supply and a transmitter/receiver 34. The device 30 is configured to transmit signals wirelessly to a smartphone device 45 carried by a carer 40 or to fixed smartphone or a tablet or a fixed device (e.g. Room Monitor) 46, or a smartwatch 47.

The device 30 includes an on-board memory and power supply in addition to a processor 32 and transmitter/receiver 34. The memory has a relatively small capacity in order to keep the cost of the device 30 as low as possible. As such the device 30 has a limited capacity to store data generated by the processor that is indicative of the electrical properties of the sensor 100 that are monitored by the device 30. Furthermore, because the memory and the power supply on the device 30 have relatively small capacities, the device 30 is configured to transmit data wirelessly and in small data packets over short distances, preferably to a smartphone device 45 or a tablet or a fixed device (e.g. Room Monitor) 46, or a smartwatch 47, that are near or come near the device 30. Preferably, the transmitter/receiver 34 is configured to transmit and receive data wirelessly using the Bluetooth standard.

The receiving device, namely the smartphone device 45 or a tablet or a fixed device (e.g. Room Monitor) 46, or a smartwatch 47 are remotely located from the transmitting device 30 and are configured to receive data via the Bluetooth standard. The transmitting device 30 is configured to transmit data in a form that can be received by any receiving device 45, 46, 47 executing an application that allows for the reception of the data via the Bluetooth standard without requiring the transmitting device 30 and the receiving devices 45, 46, 47 to be paired.

Since the memory of the transmitting device 30 is limited, or the transmission packet size is limited, the device 30 cannot store all of the data that it collects. The device 30 is configured to process the data indicative of the electrical behaviour of the first and second sets of electrodes 110, 112 of the sensor 100 and determine what information is relevant to determine the status of the absorbent article 25, for example the cumulative volume of wetness present in the absorbent article from multiple incontinence events, the presence of faecal matter in the absorbent article, the times when incontinence events occur, or the volume of each individual incontinence event. The device 30 is configured to only store, further analyse or transmit data that is deemed to be relevant to determine the status. Alternatively, the device 30 may carry out no or minimal pre-processing and may send raw time-based sensor data to any one or more receiving devices 45, 46 or 47 for storage and further processing.

In an embodiment, the processor 32 is configured to process the data indicative of the electrical behaviour of the first and second sets of electrodes 110, 112 of the sensor 100 to determine critical data and/or trend in the data such as by regression analysis or a combination of both. In an embodiment, the memory of the device 30 will only store data, referred to herein as critical data, if the value of the data has changed or varied substantially from the trend of the data or from previously stored or detected data points. Accordingly, the device 30 will store data trends and will update or add to the data trends only when necessary. The critical data and/or any trends in the data or a combination of both can be stored or further processing to determine the wetness status of the absorbent article (i.e. the cumulative volume of wetness in the absorbent article), the times when incontinence events occur, or the volume of each incontinence event or combinations thererof. As illustrated in FIG. 7, the further processing can be carried out in the device 30, in another device such as the receiving device 45, 46, 47 or in a remote server 90 after the device 30 has transmitted the data, or may be distributed between the processors in the system 10 in any combination thereof.

The device 30 is deliberately designed for low power consumption. To this end, the device employs a memory of relatively limited capacity, the processor 32 has relatively limited computational power, the device 30 is configured for relatively low frequency data sampling or sensing (i.e. in the order seconds rather than small fractions of a second). The device 30 is preferably configured for relatively low frequency data sampling, such as every few seconds or even minutes, in relation to the resistance based electrodes 110 located towards the inner water permeable layer 26 and the capacitance based electrodes 112 located at or towards the outer water impermeable layer 29 of the absorbent article 25. In some embodiments, the device 30 is configured for a moderately low frequency sampling rate of every 30 to 90 seconds.

The device 30 can be configured for variable frequency data sampling. The sampling frequency of the first set of electrodes 110 located at or near the inner water permeable layer 26 of the absorbent article 25, typically a resistance based sensor, increases if the device 30 determines that the electrical property of the resistance based sensor or data derived therefrom changes when compared to a trend, or changes when compared to previous data, or when an electrical property changes more than a threshold. For example, if the device 30 detects a significant change in the electrical property (e.g. resistance) of the first set of the electrodes 110, configured to detect faecal incontinence, the device 30 may be configured to increase the sampling frequency to enhance the quality or fidelity of the data generated and processed by the device 30. Similarly, if the device 30 detects a significant change in the electrical property (e.g. capacitance) of the second set of the electrodes 112, configured to detect urinary incontinence, the device 30 may be configured to increase the sampling frequency to enhance the quality or fidelity of the data generated and processed by the device 30. The device 30 may also be configured so as not to monitor or collect any data in relation to the electrical behaviour of one of the first and second sets of electrodes 110, 112 unless the device 30 determines from the electrical property of other one of the first and second sets of electrodes 110, 112 that is being monitored (e.g. a change in the electrical property) which thereby causes the device 30 to activate (i.e. wake up) and to collect data from one of both of the first and second sets of electrodes 110, 112. In another embodiment, the wake state of the device 30 continues for a set period of time or until the change in electrical property of the first and or second set of electrodes 110, 112 follows a trend or becomes marginal.

Also, the device 30 employs a data transmission technique involving the transfer of limited packet sizes, in particular a low energy Bluetooth (BLE) system on chip (SoC) configuration. The abovementioned features contribute towards the device 30 having relatively low power consumption characteristics and enable the device 30 to exhibit a long battery life of up to a number of months (e.g. 6 months). Accordingly, the device 30 does not require regular recharging and is inexpensive enough to manufacture that it can be disposable once the battery life has expired, however device 30 is preferably designed to allow replacement of the battery and thereby provide multi-year use. Also, because the sensors 100 are relatively inexpensive to manufacture they can be deployed into absorbent articles 25 without any substantial addition to the cost of production. The combination of these factors mean that, in practice, the system 10 and the combination of the wearable device 30 and sensors 100 represent a cost effective, everyday incontinence monitoring solution.

In some of the above and in further embodiments, the device 30 is configured with sleep and deep sleep modes or other power-down modes or statuses to further reduce the total power consumption of the device 30.

Although the device 30 is deliberately configured for obtaining, storing, processing and transmitting relatively low resolution information, the system 10 is capable of collecting data over a relatively long period of time and, indeed is intended for the full-time use and collection of data, such that even data of such low resolution can be analysed to determine patterns of incontinence of individual subjects or in categories of subjects. The determined pattern can be used as a predictive tool for defining when a subject is likely to require their absorbent article 25 to be changed or may require toileting.

The data collected by the system 10 can be used for assessment purposes, that is to determine a toileting schedule which related to when is the best time to toilet a subject 20. However, the data collected by the system 10 can also be used for predictive modelling, that is determining the urinary or faecal voiding or incontinence habits (i.e. volumes and times) of the wearer and predict when the subject 20 needs toileting or when the subject's absorbent article 25 needs to be changed. When the system 10 has established the urinary or faecal voiding or incontinence habits of the subject even if the critical data and/or the one or more data trends is not received from the device 30 by another device in the system 10, such as any one of the receiving devices 45, 46, 47, a carer can be still notified when the system 10 determines when is the best time to change the absorbent article 25 worn by a subject. The system 10 can also be configured to predict, based on historical data, when an absorbent article 25 will be saturated if data from the device 30 and sensor 100 combination are not available.

The system 10 is advantageous in that critical data and/or trend information collected over a period of time can be analysed to provide health benefits to the subjects 20 and/or economic benefits such as by determining accurate toileting patterns and determining the best time to change an absorbent article 25. Such benefits include minimising a subject's exposure to soaked absorbent articles 25, minimising damage to the skin of the subject, minimize the risk of leakage of absorbent articles 25, minimize absorbent article 25 wastage due to incorrect changing (e.g. changing a dry, or not yet full, absorbent article), labour savings due to minimising unnecessary changing or checking of absorbent articles 25, minimizing the risk of falls which can occur if subjects are not toileted or changed appropriately thus encouraging them to toilet themselves without assistance.

In embodiments of the invention described above, the processor 32 is configured to process the data indicative of the electrical behaviour of the sensor 100 to determine critical data and/or trend in the data such as by regression analysis or a combination of both. It is to be appreciated that some or all of this processing may occur in a processing device located remotely from the processor 32 on board the device 30, such as in a processer in the carer's smartphone 45 or in a fixed device in the care facility 80 or in the remote server 90. Furthermore, the method of processing the data may be a generalized regression analysis method since there is a plurality of sensor data, each obtained from each time the sensor 100 is used in an absorbent article 25. Another embodiment employs one or more clustering methods such as K-mean to determine when the incontinence or voiding events have occurred over a period of time with successive sensor 100 and absorbent article 25 combinations.

Additionally, information such as the relative mobility of a subject and user defined parameters such as a preferred number of toiletings, a preferred number of absorbent article 25 changes, preferred absorbent article 25 capacities, the number of available carers at any given time, times that the toileting or pad changes are not (or less) preferred (e.g. carers and/or wearers may not prefer to be disturbed at night) or are more preferred, can be provided to the system 10 to provide a better quality assessment of the subject's toileting or incontinence requirements or care plan.

Embodiments of the invention are advantageous in that they can enable optimising the efficiency of care staff when managing many patients. The system achieves this by providing a real time and optimally prioritised care schedule based on wetness sensor data received from absorbent article 25 and device 30 combinations and also from historical data. The prioritisation will take into account, degree of wetness in an absorbent article 25, how long the wetness has been present in the absorbent article 25 and the proximity of the subject to the carer 40. Prioritisation employs one or more triaging algorithms to classify urgency and staff level. The system 10 will keep track of how often absorbent articles 25 are changed and at what times and can assist in adjusting carer availabilities (i.e. staff levels and capability).

For example, the following is a prioritization algorithm configured to prioritize for according to highest to lowest priority:
Immediate: Saturation threshold of an absorbent article 25 has been reached
Urgent: Sensor 100 needs to be re-read/checked
Not Urgent: Saturation level of absorbent article 25 (most to least wet)

The system 10 is operable to provide carers with ample warning to change an absorbent article 25 whilst reducing the risk of leakage and skin problems by using recently acquired data from the sensor 100 and device 30 combination as well as historical data whereby both the carer and the subject can calculate a grace period for a time to change alert. The system can allow for data collected by the carer at the time of changing an absorbent article to provide feedback for the system. For example, if at time of change the absorbent article 25 has already leaked then this information can be fed into the system 10 which can determine that the grace period is insufficient. On the other hand, if at time of change the absorbent article 25 is dry or has not reached capacity then this information can be fed into the system 10 which can determine that the grace period is should be increased.

In another embodiment, the system 10 can employ a risk rating. In this embodiment, the system calculates a risk that the absorbent article 25 of a subject requires changing based on a risk matrix with saturation of the absorbent article 25 as determined by the system 10 from data from the wetness sensor 100 and device 30 combination. Accordingly, the system 10 calculates a risk that an absorbent article 25 may have leaked or may be about to leak is considered to be a function of these variables and provides an appropriate alert to the carer according to a setting (e.g. threshold setting) in the system 10.

Other advantages of embodiments of the invention include that it provides greater reliability in terms of notifying carers of the correct time to change an absorbent article 25 and the consequent reduction of false positives by using individual historical data to validate sensor readings and notification timings.

Some embodiments of the system 10 provide an alert function to notify a carer to change an absorbent article without requiring the carer to carry a smartphone 45. This is achieved by providing a fixed or stationary device or room monitor as illustrated in FIGS. 5 and 7. In this embodiment, the system 10 provides an alert when a device 30, within a proximity, detects an electrical property of wetness sensors 100 in an absorbent article 25 that exceeds a given threshold. The room monitor may provide an obvious signal such as a change of colour to represent the wetness status of the absorbent article 25. The fixed device can display the wetness status of multiple absorbent articles 25 worn by multiple subjects in the vicinity of the fixed device at a given time. The fixed device embodiment can be employed in hospital or aged care facility rooms shared by multiple subjects and in child care facilities.

In another embodiment, as illustrated in FIG. 6, the system 10 provides an alert function to notify a carer via their smartphone 45 or smartwatch 47. In this embodiment, the system 10 provides an alert when a device 30 worn by a subject comes within a proximity of the carers smartphone 45 or smartwatch 47 and where data transmitted from the device 30 indicates the an absorbent article 25 requires changing. The smartphone 45 or smartwatch 47 preferably executes an application that is adapted to display the status of any device 30 and sensor 100 combination worn by a subject in proximity such as whether or not the absorbent article 25 contains urine or faecal matter and whether the absorbent article does, or does not require changing. Other information may be displayed such as how long the absorbent article 25 has been worn by the subject as this may also be a factor that determines if it is time to change the article. In yet another embodiment, alert notification may be delivered by a pre-existing notification system, such as nurse call systems used on aged care centres, hospitals and the like.

As illustrated in FIG. 5, the smartphone 45, fixed device 46 or smartwatch 47 is preferably configured, such as by software executed in the device, to provide an obvious signal such as a change of colour on a display of the device to represent the status of the absorbent article 25. The smartphone 45, fixed device 46 or smartwatch 47 device can display the status of multiple absorbent articles 25 worn by multiple subjects in the vicinity of the smartphone 45, fixed device 46 or smartwatch 47 at a given time. The fixed device embodiment can be employed in hospital or aged care facility rooms shared by multiple subjects and in child care facilities. Also, because the transmitting device 30 and the smartphone 45, fixed device 46 or smartwatch 47 are configured to transmit and receive data via the Bluetooth standard in a non-paired configuration any smartphone 45, fixed device 46 or smartwatch 47 in the vicinity of any of the transmitting device 30 and the absorbent pad 25 combinations will be capable of providing a notification of the status of the absorbent pad 25, as illustrated in FIG. 6.

In another embodiment, the device 30 can include an accelerometer producing data that can be used to assess mobility and risk of falls. This data can be included in toileting and care planning and scheduling to improving the efficiency of absorbent article 25 changing and toileting activities. Also, the device 30 may enable Bluetooth positioning and/or tracking data to create a movement behavioural dataset for assessment. Furthermore, Bluetooth positioning and/or tracking data can be used to generate an alert when a subject has wandered into a prohibited zone, or out of a desired zone. In another embodiment, detection and analysis of movement and positioning can be useful in the detection of lack of movement of infants and potentially provide a warning or indication of a risk of sudden infant death syndrome. In a further embodiment, detection and analysis of movement and positioning can be useful in relation to the prevention pressure ulcer development and wound management in the elderly. In a further embodiment, detection and analysis of movement and positioning can be useful in relation to the detection and prevention of cognitive decline in the elderly based on analysis of movement against a baseline or standard. In a further embodiment, detection and analysis of movement and positioning can be useful in relation to the detection and prevention of falls in the elderly. In a further embodiment, detection and analysis of movement and positioning can be useful in relation to the determination of a risk of falling based on pattern recognition and detection against a baseline or standard.

The device 30 preferably also includes a thermistor or other like temperature sensor adapted for sensing temperature. The thermistor or other like temperature sensor is operable to detect and monitor environmental temperatures which can be useful for the detection of risk factors and potentially aid in the prevention of sudden infant death syndrome in infants.

The low cost of the manufactured sensor 100 and wearable device 30 make it possible for the system to be used to address applications that would not been considered economically viable for the utilization of sensor-enabled urinary or faecal event detection and monitoring. One of these very cost-sensitive fields of application is the field of 24/7 incontinence management. Another example is the field of childcare and indeed any setting in which a subject is required to wear an incontinence garment or pad for any reason.

As detailed above, the incontinence management system 10 monitors the ingress of fluid or other urine or faecal constituents associated with an incontinence event into an absorbent article 25 and processes the data to determine wetness status data, or other data, indicative of an amount of fluid or other urine or faecal constituents present in the absorbent article 25. Other data such as the time of an incontinence event and volume or quantity of liquid associated with individual incontinence events. The wetness status data, time of incontinence event data and volume or quantity of incontinence event data for a subject is stored as chronological incontinence data and is processed to determine a care plan for the subject. The chronological incontinence data, or historical incontinence data, is processed automatically or interactively to determine the care plan for the subject. The wetness status data, time of incontinence event data and volume or quantity of incontinence event data is stored in the device connected to the electrodes and is transmitted to another data storage location where the data related to a particular subject is additively stored.

Preferably, the device 30, or any other device within the system 10 such as the smartphone 45, fixed device 46 or smartwatch 47, as illustrated in FIG. 5 or in the remote cloud based server 90 as illustrated in FIG. 7, processes the data indicative of the electrical property to determine critical data which is indicative of a measure such as the presence of wetness and/or the time and/or a volume of wetness and/or a cumulative volume of a sequence of wetness events and/or data indicative of one or more trends, such as is determined by regression analysis.

In embodiments, data that is generated by the system 10 can be stored and processed either in any device within the system 10 such as the wearable device 30, smartphone 45, fixed device 46, smartwatch 47, as illustrated in FIG. 5 or in the remote cloud based server 90 as illustrated in FIG. 7. Such historical data from the capacitance based sensor can be processed for assessment, care planning and scheduling purposes. Data collected over time for a person is analysed to determine when a subject needs toileting or a pad change. For example, if historical data shows that for a particular subject a pad change is required at about 4 pm, daily, then this pad change time can be included in a care plan prepared for the subject. In another example the historical data can be used to determine an optimum time of the day to toilet the subject, the most appropriate or optimal pad size to be used, the subject's hydration level, and also in diagnosing urinary tract infection.

In another embodiment, the historical data can be processed to determine how a subject's incontinence level, fluid output level, or hydration health compared to other members in the subject's demographic. In another embodiment, in particular where data is provided by the system to the cloud based server 90, the historical data of a care facility can be compared to data collected from other care facilities to determine an average level of incontinent subject's resident in that care facility; or the hydration health of the subject's resident in that facility compared to other care facilities.

As illustrated in FIG. 7, data collected and processed by the cloud based server 90 in relation to one or more users of the system 10 in one location can be provided to external servers 150 for other external purposes (e.g. for information for payers, inventory management, regulatory compliance).

In another embodiment the historical data of an incontinent subject can be used to determine a bench-mark for the subject. For example if the wetness status data collected from an absorbent article worn by a subject shows an abnormality, in comparison with historical data collected in relation to the subject, then the system can notify a carer, such as by issuing an alert to a carer, to attend to the subject and perform a further investigation or tests to determine a reason for the abnormality. For example if the historical data shows an average of 4 pad changes in a given period for a particular subject (with, for example, the maximum number of pad changes for the subject over previous periods of the same duration being 7 and the minimum being 3), but during an equivalent period the system only directs a carer to make two pad changes then there is possibility that the subject is dehydrated or may have become less incontinent. In another example, if the system directs a carer to make more than the maximum number of pad changes in the historical data then this may indicate that the subject has a urinary tract infection or some other health issue or they are wearing an absorbent article with a smaller capacity than is required.

Preferably, the abnormality function is determined by the application of any one or more of a statistical outlier detection function or a statistical function that considers standard deviations of historical data, mean and average of historical data, comparison to the trend of the historical data, comparison to the upper band and lower band of the historical data. In an embodiment a mixed model regression analysis can be utilized to detect the abnormalities.

The invention may be susceptible to other modifications or mechanical equivalents without departing from the spirit or ambit of the invention disclosed herein.

The invention claimed is:

1. An incontinence monitoring system, the incontinence monitoring system comprising:
  a plurality of electrodes on an absorbent article including an absorbent core; and
  a device for electrical connection with the plurality of electrodes and monitoring one or more electrical properties of the plurality of electrodes;
  wherein a first set of the plurality of electrodes are adapted for detection of wetness associated with urinary incontinence events disposed on a surface of a water impermeable layer of the absorbent article facing away from a wearer with the absorbent core located on an opposite side of the water impermeable layer facing towards the wearer, and a second set of the plurality of electrodes are adapted for detection of fecal incontinence events disposed on a surface of a flexible substrate, wherein the second set of the plurality of electrodes are located on or towards an inner body facing water permeable layer,
  wherein the device includes a plurality of electrical contacts each adapted for electrical connection with an individual electrode of the plurality of electrodes in the absorbent article,
  wherein the device includes first and second sets of the plurality of electrical contacts that are adapted to engage from opposite sides of the first and second sets of the plurality of electrodes disposed on opposite surfaces of the absorbent article,
  wherein relative to a longitudinal direction of the plurality of the electrodes, each of the plurality of the electrical contacts of the first and second sets are positioned adjacent to each other in a transverse direction so as not to overlap in the longitudinal direction with any of the other electrical contacts of the plurality of electrical contacts in the same set, and wherein the plurality of electrical contacts located consecutively in the transverse direction alternate between the plurality of electrodes of the first and second sets.

2. The system of claim 1, wherein the first set of the plurality of electrodes exhibit a change in capacitance upon ingress of fluid from the urinary incontinence events.

3. The system of claim 1, wherein the first set of the plurality of electrodes comprise at least two mutually separated flexible conductive electrodes.

4. The system of claim 1, wherein the second set of plurality of electrodes are adapted to exhibit a change in capacitance, resistance or impedance in the presence of constituents of the fecal incontinence events.

5. The system of claim 1, wherein the second set of the plurality of electrodes comprise at least two flexible conductive electrodes disposed on the surface of the flexible substrate, wherein the second set of the plurality of electrodes are adapted to exhibit a change in capacitance, resistance or impedance in the presence of constituents of the fecal incontinence events.

6. The system of claim 1, wherein the each individual electrode of the plurality of electrodes is adapted for electrical connection with an individual electrical contact of the plurality of electrical contacts of the device for the monitoring the electrical property of the plurality of electrodes.

7. The system of claim 6, wherein the plurality of electrodes each include a contact portion adapted for electrical connection with the individual electrical contact of the plurality of electrical contacts of the device, wherein the contact portions of the plurality of electrodes are positioned to not overlap with each other.

8. The system of claim 1, wherein at least some of the plurality of electrical contacts of the device are adapted to engage the plurality of electrodes from one direction and are positioned adjacent to each other in the transverse direction and not overlapping in the longitudinal direction of the plurality of electrodes.

9. The system of claim 1, wherein the first and second sets of the plurality of electrical contacts are disposed on opposing surfaces of a housing of the device adapted to receive and clamp down on the absorbent article and the first and second sets of the plurality of electrodes therebetween.

10. The system of claim 1, wherein the absorbent article includes:
- a water permeable cover sheet facing towards the wearer;
- a water impermeable backing sheet facing away from the wearer;
- the absorbent core positioned between the cover sheet and the backing sheet;
- the first set of the plurality of electrodes being located on a surface of the water impermeable backing sheet with the absorbent core on an opposite side of the water impermeable backing sheet; and the second set of electrodes being located on or near the water permeable cover sheet.

* * * * *